(12) United States Patent
Landru (10) Patent No.: US 8,429,960 B2
(45) Date of Patent: Apr. 30, 2013

(54) PROCESS FOR MEASURING AN ADHESION ENERGY, AND ASSOCIATED SUBSTRATES

(75) Inventor: Didier Landru, Champ Pres Froges (FR)

(73) Assignee: Soitec, Bernin (FR)

( * ) Notice: Subject to any disclaimer, the term of this patent is extended or adjusted under 35 U.S.C. 154(b) by 141 days.

(21) Appl. No.: 12/910,023

(22) Filed: Oct. 22, 2010

(65) Prior Publication Data
US 2012/0048007 A1    Mar. 1, 2012

(30) Foreign Application Priority Data

Aug. 24, 2010 (FR) .................................... 10 56719

(51) Int. Cl.
*G01N 19/04* (2006.01)
*G01N 3/08* (2006.01)
*G01L 1/00* (2006.01)

(52) U.S. Cl.
USPC ............... 73/150 A; 73/760; 73/785; 73/826; 73/827

(58) Field of Classification Search ................. 73/150 A
See application file for complete search history.

(56) References Cited

U.S. PATENT DOCUMENTS

| | | | |
|---|---|---|---|
| 5,223,001 A | 6/1993 | Saeki | 29/25.01 |
| 5,537,884 A | 7/1996 | Nishimura et al. | 73/842 |
| 5,696,327 A | 12/1997 | Huang et al. | 73/845 |
| 5,834,812 A | 11/1998 | Golland et al. | 257/347 |
| 5,937,312 A | 8/1999 | Iyer et al. | 438/459 |
| 6,008,113 A | 12/1999 | Ismail et al. | 438/615 |
| 6,113,721 A | 9/2000 | d'Aragona et al. | 156/154 |
| 6,117,695 A | 9/2000 | Murphy et al. | 438/15 |
| 6,180,496 B1 | 1/2001 | Farrens et al. | 438/455 |
| 6,207,005 B1 | 3/2001 | Henley et al. | 156/345 |
| 6,221,774 B1 | 4/2001 | Malik | 438/690 |
| 6,347,284 B1 * | 2/2002 | Ohira et al. | 702/41 |
| 6,387,815 B2 | 5/2002 | Sakamoto | 438/709 |

(Continued)

FOREIGN PATENT DOCUMENTS

| | | |
|---|---|---|
| EP | 0 366 208 A2 | 5/1990 |
| EP | 0 444 942 B1 | 9/1991 |

(Continued)

OTHER PUBLICATIONS

Preliminary Search Report and Written Opinion with English Translation for Application FR 1056719 dated Apr. 12, 2011.

(Continued)

*Primary Examiner* — Andre Allen
(74) *Attorney, Agent, or Firm* — Winston & Strawn LLP (57) ABSTRACT

The invention relates to a structure and a process for measuring an energy of adhesion between two substrates bonded in a transverse direction. The method involves providing for at least one of the two substrates to have a plurality of elementary test cells within a test layer each being capable of locally applying, in the transverse direction, a preset mechanical stress ($\sigma$), dependent on the temperature (T), to a bond interface between the substrates in a direction tending to separate them, applying a test temperature to the substrates and identifying debonded regions of the bond interface so that the local adhesion energy at the test temperature in the regions may be deduced therefrom, the local adhesion energy in a region of the bond interface being deduced from the stress applied by the test cells that caused debonding in the region.

19 Claims, 4 Drawing Sheets

U.S. PATENT DOCUMENTS

| | | |
|---|---|---|
| 6,523,419 B1 | 2/2003 | Nonaka et al. ............... 73/827 |
| 6,616,332 B1 | 9/2003 | Renken et al. ............. 374/162 |
| 6,645,828 B1 | 11/2003 | Farrens et al. ............. 438/455 |
| 6,908,832 B2 | 6/2005 | Farrens et al. ............. 438/455 |
| 7,250,368 B2 | 7/2007 | Kida et al. ................. 438/690 |
| 7,727,860 B2 | 6/2010 | Miyazaki et al. ........... 438/459 |
| 2001/0055863 A1 | 12/2001 | Nakano et al. ............. 438/549 |
| 2002/0187595 A1 | 12/2002 | Walitzki et al. ............ 438/184 |
| 2002/0194930 A1* | 12/2002 | Crosby et al. ................. 73/827 |
| 2003/0079828 A1 | 5/2003 | Kassir et al. ............... 156/230 |
| 2003/0168145 A1 | 9/2003 | Suga et al. .................. 156/60 |
| 2004/0074293 A1* | 4/2004 | Pundt et al. ................ 73/150 A |
| 2004/0085858 A1 | 5/2004 | Khuri-Yakub et al. ..... 367/181 |
| 2004/0121556 A1 | 6/2004 | Kim et al. ................... 438/455 |
| 2004/0229444 A1 | 11/2004 | Couillard et al. ........... 438/455 |
| 2004/0246795 A1 | 12/2004 | Tomita ........................ 365/200 |
| 2005/0081958 A1 | 4/2005 | Adachi et al. .............. 148/33.1 |
| 2005/0152089 A1 | 7/2005 | Matsuda et al. ............ 361/234 |
| 2006/0055003 A1 | 3/2006 | Tomita et al. .............. 257/629 |
| 2006/0065909 A1* | 3/2006 | Wong et al. ................ 257/192 |
| 2007/0039395 A1 | 2/2007 | Gupta et al. ................ 73/800 |
| 2007/0072393 A1 | 3/2007 | Aspar et al. ................. 438/459 |
| 2007/0117229 A1 | 5/2007 | Schwarzenbach et al. ..... 438/14 |
| 2007/0158831 A1 | 7/2007 | Cha et al. ................... 257/724 |
| 2007/0237448 A1 | 10/2007 | Sato et al. .................. 385/13 |
| 2008/0044984 A1 | 2/2008 | Hsieh et al. ................ 438/458 |
| 2008/0053619 A1 | 3/2008 | Nakayama et al. ......... 156/382 |
| 2008/0128621 A1 | 6/2008 | Berry ........................ 250/338.1 |
| 2008/0128898 A1 | 6/2008 | Henderson et al. ......... 257/713 |
| 2008/0200008 A1 | 8/2008 | Kerdiles et al. ............ 438/455 |
| 2009/0023271 A1 | 1/2009 | Couillard et al. ........... 438/458 |
| 2009/0042363 A1 | 2/2009 | Miyazaki et al. ........... 438/459 |
| 2009/0111245 A1 | 4/2009 | Okabe et al. ............... 438/459 |
| 2010/0122762 A1 | 5/2010 | George ........................ 156/64 |
| 2010/0155882 A1 | 6/2010 | Castex ........................ 257/507 |
| 2011/0045611 A1 | 2/2011 | Castex et al. ................... 438/5 |
| 2011/0097874 A1 | 4/2011 | Broekaart et al. .......... 438/459 |
| 2011/0308721 A1 | 12/2011 | Broekaart et al. .......... 156/285 |
| 2012/0038027 A1 | 2/2012 | Broekaart ................... 257/618 |

FOREIGN PATENT DOCUMENTS

| | | |
|---|---|---|
| EP | 0 451 993 A2 | 10/1991 |
| EP | 0 854 500 B1 | 7/1998 |
| EP | 0 860 862 B1 | 8/1998 |
| EP | 0 935 280 B1 | 8/1999 |
| EP | 0 964 436 A2 | 12/1999 |
| EP | 1 189 266 A1 | 3/2002 |
| EP | 1 662 549 A1 | 5/2006 |
| EP | 1 887 613 A1 | 2/2008 |
| EP | 1 998 368 A2 | 12/2008 |
| EP | 2 200 077 A1 | 6/2010 |
| FR | 2 935 535 A1 | 3/2010 |
| JP | 3089519 B2 | 4/1991 |
| JP | 4263425 A | 9/1992 |
| JP | 7045485 A | 2/1995 |
| JP | 9017984 A | 1/1997 |
| JP | 11017701 A | 1/1999 |
| JP | 11067701 A | 3/1999 |
| JP | 11354761 A | 12/1999 |
| JP | 2001144274 A | 5/2001 |
| WO | WO 99/60607 A2 | 11/1999 |
| WO | WO 03/008938 A2 | 1/2003 |
| WO | WO 03/019157 A1 | 3/2003 |

OTHER PUBLICATIONS

Takagi et al., "Room Temperature Silicon Wafer Direct Bonding in Vacuum by Ar Beam Irradiation," Micro Electro Mechanical Systems, 1997, MEMS '97, Proceedings, IEEE, Tenth Annual International Workshop on Jan. 26-30, 1997, Nagoya, Japan, pp. 191-196. Online search, URL: http://ieeexplore.ieee.org/stamp/stamp.jsp?tp=&arnumber=581801.

W.P. Maszara, et al., "Bonding of Silicon Wafers for Silicon-on-Insulator", J. Appl. Phys., vol. 64, No. 10, pp. 4943-4950, (1988.

European Search Report, French Appln. No. 1002618, dated Jan. 25, 2011.

International Search Report, PCT/EP2009/059961, mailed Oct. 5, 2009.

European Search Report for EP08291226 dated Jul. 7, 2009.

Andreas Plößl et al., "Covalent Silicon Bonding at Room Temperature in Ultra High Vacuum", Mat. Res. Soc. Symp. Proc., vol. 483, pp. 141-146, Materials Research Society (1998).

Hideki Takagi et al, "Wafer-Scale Spontaneous Bonding of Silicon Wafers by Argon-Beam Surface Activation at Room Temperature", Sensors and Actuators A, vol. 105, pp. 98-102 (2003).

R. H. Esser et al., "Improved Low-Temperature Si-Si Hydrophilic Wafer Bonding", Journal of The Electrochemical Society, vol. 150, pp. G228-G231 (2003).

Burns, James A. et al., "A Wafer-Scale 3-D Circuit Integration Technology", IEEE Transactions on Electron Devices, vol. 53, No. 10, pp. 2507-2516 (2006).

Steen, Steven E. et al., "Overlay as the Key to Drive Wafer Scale 3D Integration", Microelectronic Engineering, vol. 84, pp. 1412-1415 (2007).

Topol, Anna W. et al., "3D Fabrication Options for High-Performance CMOS Technology", Wafer Level 3 ICs Process Technology, Tan, Gutmann, Reif Eds., pp. 197-217. (2008).

Gosele, U. et al., "Self-Propagating Room-Temperature Silicon Wafer Bonding in Ultrahigh Vacuum", Applied Phys. Lett., vol. 67, No. 24, pp. 3614-3615 (1995).

* cited by examiner

PROCESS FOR MEASURING AN ADHESION ENERGY, AND ASSOCIATED SUBSTRATES

FIELD OF THE INVENTION

The invention relates to a process for measuring an energy of adhesion between substrates to be bonded. The invention also relates to a substrate for measuring such an adhesion energy and to a structure comprising such a substrate. The invention has numerous applications and particularly in the electronics, microelectronics or optics fields.

BACKGROUND OF THE INVENTION

In the electronics and microelectronics field it is common to use a step of bonding two substrates together. This type of bonding is for example used to fabricate SOI (silicon-on-insulator) substrates or for 3D integration of substrates comprising electronic circuits that are to be connected.

It is generally necessary to evaluate the bond quality which is characterized in particular by the adhesion energy, also called the bonding energy, of the bond between the surfaces of two substrates.

Various metrology processes have been proposed in the prior art for characterizing this adhesion energy.

A traction-test process is known from the prior art, this being a process for determining the adhesion energy directly and macroscopically. However, this process is very difficult to implement.

A bond measurement process, proposed by Maszara in the document entitled "Bonding of silicon wafers for silicon-on-insulators", J. Appl. Phys. 1988, 64, 4943, is also known.

In this process, a blade is inserted at the bond interface between the two substrates. Applying a mechanical force via the blade in a direction parallel to the plane of the bond interface causes the two substrates to debond locally and the debonded region to propagate over a certain distance. The length over which the debonded region has propagated gives an indication of the energy of adhesion between the two substrates.

However, this process has several drawbacks.

This process is an indirect measurement of the adhesion energy since it is extrapolated from the propagation of the interface debond. The quantity measured is therefore the tear strength of an interface rather than the adhesion energy itself.

Furthermore, this process is dependent on the blade insertion conditions and on the operator, which make it an imprecise process.

In addition, this process is macroscopic, that is to say that it allows only an average adhesion energy to be determined over a significant area, rather than a local adhesion energy.

Finally, this process is implemented at room temperature and therefore characterizes the adhesion energy only at room temperature.

It is therefore clear that the processes of the prior art for measuring an adhesion energy have numerous drawbacks.

SUMMARY OF THE INVENTION

The present invention relates to a structure capable of measuring an energy of adhesion between itself and another substrate at a bond interface, and to a process for measuring an energy of adhesion between two bonded substrates using such a structure.

The process of measuring an energy of adhesion between two bonded substrates comprises providing a test layer on a first substrate, wherein the test layer has an exposed surface; providing a plurality of elementary test cells within the test layer, wherein the test cells are each capable of locally applying a preset mechanical stress ($\sigma$) dependent on a temperature (T), wherein each elementary test cell within the test layer comprises two pads where both pads are made of a material that expands when heated, and further wherein each test cell applies a different preset mechanical stress ($\sigma$) at the same test temperature ($T_t$), compared to the other test cells within the test layer. The process also comprises providing bonding a second substrate to the exposed surface of test layer to form a bonding interface; and increasing the temperature (T) of the bonded substrates to up to a test temperature ($T_t$), wherein the plurality of elementary test cells apply a preset transverse tensile stress to the bond interface. The process may further include providing a bonding layer on the exposed surface of the test layer, wherein the bonding layer has an exposed surface, and bonding the second substrate to the exposed surface of the bonding layer, such that the bonding layer is between the second substrate and the test layer and test cells within the test layer.

The process may also include applying the test temperature to the substrates, wherein each of the plurality of elementary test cells apply a different preset mechanical stress ($\sigma$), at the test temperature ($T_t$) locally to the bond interface in the transverse direction at the bond interface between the substrates in a direction tending to separate the bonded surfaces; and identifying debonded regions at the bond interface associated with one or more elementary test cells applying the different preset mechanical stress ($\sigma$), such that the local adhesion energy at the test temperature in the regions may be deduced from which test cells are associated with a debonded region, in which the debonded regions of the bond interface can be identified using an acoustic microscope. The process may further comprises repeating the steps of applying a test temperature ($T_t$) to the substrates over a range of temperatures (T); and identifying the debonded regions of the bond interface at the several different test temperatures ($T_t$) in the range, so as to deduce the local adhesion energy over the range of temperatures.

The process may include having one or more test structures within the test layer, wherein a plurality of elementary test cells forms a test structure, and each test cell within the test structure applies a different preset stress at the same preset test temperature, such that the test structure indicates the local adhesion energy at the bond interface by identifying the debonded regions between one test cell and another. The test layer can comprise a plurality of test structures distributed over the surface of the first substrate so as to apply stresses to a plurality of different regions of the bond interface, wherein each test structure comprises a plurality of elementary test cells that apply a different preset mechanical stress at the same test temperature. Test cells applying the same preset mechanical stress at a preset temperature may be in each test structure.

The process can include having test cells, wherein each test cell is physically differentiated from the other test cells in a test structure by a set of parameters comprising; a preset stress applied by the cell and a preset temperature at which the stress is applied, and/or a local adhesion energy and a temperature at which the adhesion energy is reached; and the process can further comprise the step of deducing the local adhesion energy by determining which test cells with a preset set of parameters are associated with a debonded region.

The present invention also relates to a substrate capable of measuring an energy of adhesion between itself and another substrate at a bond interface comprising: a first substrate; a test layer formed on the first substrate, wherein the test layer has an exposed surface for bonding; a plurality of elementary test cells formed within the test layer, wherein each test cell is capable of locally applying in a transverse direction, a preset mechanical stress (σ) de pendent on the temperature (T), to a bond interface located between the surface of the test layer and another substrate bonded thereto. The structure may have elementary test cells within a test layer, wherein the elementary test cells are at the free surface of the test layer, such that the test cells apply the preset mechanical stress to the second substrate at the bond interface. The elementary test cell within the test layer comprise two pads, where both pads are made of a material that expands when heated.

The substrate may further comprise a second substrate bonded to the exposed surface of the test layer to form a bond interface, wherein the test layer and bond interface are at a test temperature; and locally debonded regions at the bond interface, wherein one of the debonded regions is associated with one elementary test cell applying the preset mechanical stress (σ) at the test temperature, where the preset mechanical stress is different from one elementary test cell to another at the test temperature, such that the local adhesion energy in a region may be determined by which test cell is associated with a debonded region, and wherein the debonded regions can be identified using an acoustic microscope.

In another embodiment, the substrate may further comprise a bond layer formed on the surface of the test layer, such that the bonding layer is between the second substrate and the test layer, wherein the test cells are distributed in the test layer and covered by the bond layer, and a surface of the bond layer forms the bond interface with the second substrate.

In another embodiment, the first substrate is a transparent support layer upon which the test layer and elementary test cells are formed.

The substrate may further comprise a plurality of test structures, wherein each test structure has a plurality of different elementary test cells capable of applying different mechanical stresses to a plurality of regions of the bond interface at a preset temperature. The substrate may have test cells in which each cell is physically differentiated by a set of parameters comprising a preset stress applied by the cell and a preset temperature at which the stress is applied, or a local adhesion energy and a temperature at which the energy is reached.

In another embodiment, at least the first substrate or the second substrate include electronic circuits. Also, the substrate may be associated with an acoustic microscope for identifying debonded regions The invention has many advantages. One advantage of the invention is that it provides a simple and direct measurement of the adhesion energy at a bond interface. Another advantage of the invention is that it provides a precise measurement of the adhesion energy. Yet another advantage of the invention is that it provides a local measurement of the adhesion energy. Finally, another advantage of the invention is that it provides a measurement of the adhesion energy at different temperatures.

BRIEF DESCRIPTION OF THE DRAWINGS

Other features and advantages of the invention will emerge from the following description, which is purely illustrative and non-limiting and must be read in conjunction with the appended drawings in which.

DETAILED DESCRIPTION OF THE INVENTION

The present invention proposes to alleviate the aforementioned drawbacks. For this purpose, the invention proposes a process for measuring an energy of adhesion between two substrates bonded in a transverse direction comprising the steps of providing for at least one of the two substrates to comprise a plurality of elementary test cells each being capable of locally applying, in the transverse direction, a preset mechanical stress (o), dependent on the temperature (T), to a bond interface between the substrates in a direction tending to separate them; applying a test temperature ($T_t$) to the substrates; and identifying debonded regions of the bond interface so that the local adhesion energy at the test temperature ($T_t$) in the regions may be deduced therefrom, the local adhesion energy in a region of the bond interface being deduced from the stress applied by the test cells that caused debonding in the region.

The invention is advantageously supplemented by the following features, applied individually or in any technically possible combination.

A sequence comprising the steps of applying a test temperature ($T_t$) to the substrates and identifying the debonded regions of the bond interface, is repeated in a range comprising several test temperatures ($T_t$), so as to deduce the local adhesion energy for the range of test temperatures; each elementary test cell applies a preset stress at a preset temperature during the step of applying a test temperature, the set, consisting in the preset stress and the preset temperature, being different from one cell to another; the substrate comprises a plurality of test structures distributed over a substrate, so as to apply stresses to a plurality of regions of the bond interface, each test structure comprising a plurality of different elementary test cells; where each cell is physically differentiated by a set of parameters comprising a preset stress applied by the cell and a preset temperature at which the stress is applied and/or a local adhesion energy and a temperature at which the energy is reached, the step of deducing the local adhesion energy being carried out by reading the set of parameters; and the debonded regions of the bond interface are identified using an acoustic microscope.

The invention also proposes a substrate comprising a plurality of elementary test cells each capable of locally applying, in a transverse direction, a preset mechanical stress, dependent on the temperature, to a bond interface located at a free surface of the substrate.

The substrate may furthermore comprise at least one of the following features: each elementary test cell is capable of applying a preset stress at a preset temperature, the set, consisting in the preset stress and the preset temperature, being different from one cell to another; the elementary test cells are distributed in a test layer placed beneath a bond layer a free surface of which forms the bond interface; the elementary test cells are placed at the free surface of the substrate; the substrate comprises a plurality of test structures capable of applying stresses to a plurality of regions of the bond interface, each test structure comprising a plurality of different elementary test cells; each cell is physically differentiated by a set of parameters comprising a preset stress applied by the cell and a preset temperature at which the stress is applied, and/or a local adhesion energy and a temperature at which the energy is reached; and the substrate comprises a transparent support layer beneath the test layer.

The invention also proposes a structure comprising the substrate described above and a second substrate bonded to the substrate at the bond interface. In one embodiment, the substrate and the second substrate (1,8) at least comprises electronic circuits.

The following non-limiting examples of preferred embodiments are provide in reference to the accompanying drawings to further highlight the features and advantages of the present invention. It is understood that such embodiments do not represent the full scope of the invention, for which reference should be made to the claims.

Figure 1:
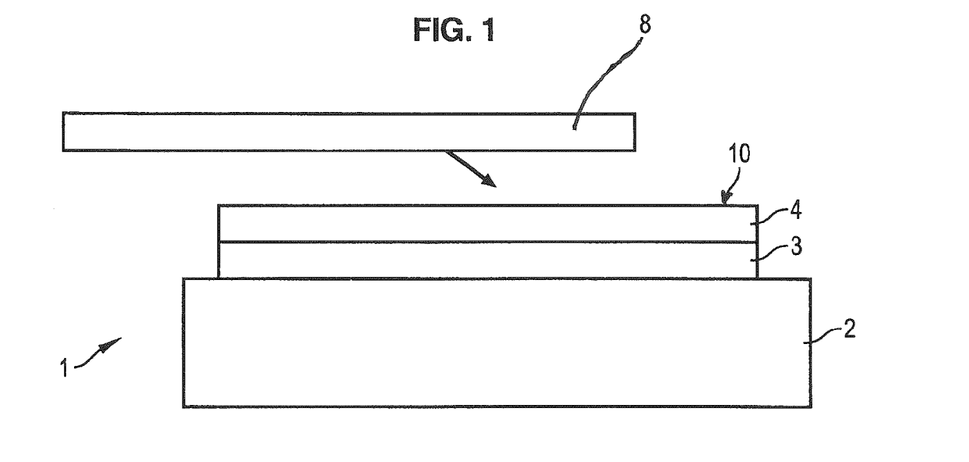
FIG. 1 shows an embodiment of a substrate according to a first aspect of the invention.

FIG. 1 shows a preferred embodiment of a substrate 1, also referred to as a layered structure, according to one example of the invention. The substrates to be bonded 2, 8 may be of any type, such as, for example, silicon-on-insulator (SOI) substrates. The substrate 1 comprises a bond layer 4, on one of its faces, intended to be bonded to a second substrate 8. The bond layer 4 is for example an oxide layer. The substrate 1 furthermore comprises at least one test layer 3 placed beneath the bond layer 4. The bonding is produced in a transverse direction collinear to the vector perpendicular to the plane of the substrates 1, 8 when bonded.

The substrate 1 comprises in general a first substrate or support substrate 2 placed beneath the test layer 3. The support substrate 2 is for example made of silicon. It is clear that the substrate 1 may comprise additional layers or elements depending on the requirements and applications to form a layered structure. In addition, the first substrate 1 and/or the second substrate 8 may include electrical circuits in the conventional context 3D integration.

In an alternate embodiment (not shown), the substrate 1 does not include a bonding layer 4, so that the test layer 3 is formed on the first substrate and has an exposed surface for bonding to the second substrate 8.

The bond interface 10 is the interface at which the bond between the surfaces of substrate 1 and the substrate 8 is formed. In particular, the bond interface 10 is located at a free surface of either the bond layer 4, or the test layer 3 when the bond layer is not present.

In the preferred embodiment, a particular advantage of the invention is that the cells 6 may be buried, that is to say that they are placed not at the bond interface 10 or in the bond layer 4 but, for example, in the test layer 3 located beneath the bond layer 4, a free surface of which forms the bond interface. This enables a homogenous bond layer 4 to be obtained and avoids disturbing the operations for treating the bond layer 4, in particular the free surface of the bond layer 4. The local adhesion energy can therefore be measured without disturbing or damaging the bond interface, and in particular the free surface of the bond layer. Many drawbacks and limitations of the processes and devices of the prior art are thus avoided.

Figure 2:
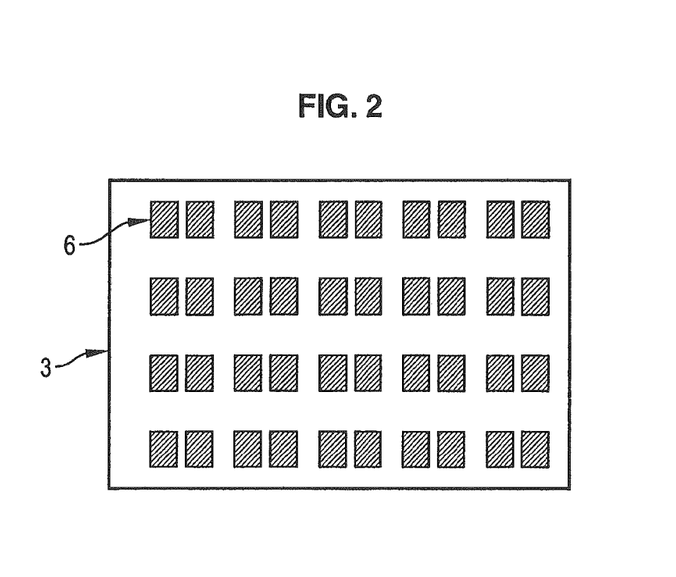
FIG. 2 shows an embodiment of a plurality of elementary test cells used in the substrate of FIG. 1.

As shown in FIG. 2, the test layer 3 is in particular characterized in that it comprises a plurality of elementary test cells 6. The test elements are within the test layer, and the test cells may be flush with the free surface.

Figure 3:
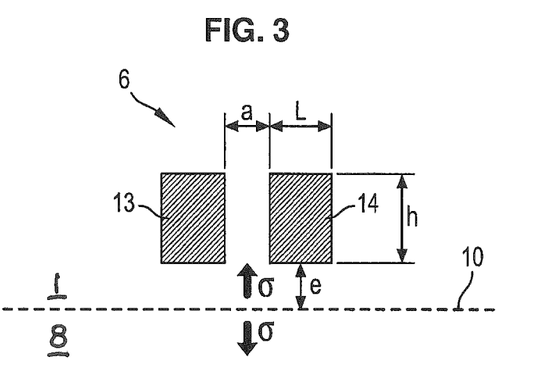
FIG. 3 shows an embodiment of an elementary test cell.

As shown in FIG. 3, the each cell 6 comprises two pads 13, 14 of a material, such as copper, that expands when heated. By "pad" a generally cube shaped or parallelepiped shaped structure is meant. In general, the material of each cell is chosen to have a thermal expansion coefficient different from thermal expansion coefficient of the test layer 3. Each cell 6 being capable of applying locally, in the transverse direction, where the transverse direction is understood to be perpendicular to the plane of a bonding interface between the substrates, a preset mechanical stress σ to a bond interface 10 located between the substrate 1 and the substrate 8. This stress depends on the temperature T applied to the substrate 1 and is directed transversely in a direction tending to separate the bonded surfaces of substrate 1 and 8. In other words, the cells 6 are sized to apply a tensile stress σ to the bond interface 10, as depicted in FIG. 3.

The stress σ applied by each cell depends on the temperature and the dimensions of the cell. In the case of the pads 13, 14 shown in FIG. 3, the stress applied by the cell 6 also depends on the spacing 'a' between the pads, on the width 'L' of the pads, on the transverse height 'h' of the pads, and on the distance 'e' relative to the bond interface 10. For example, the cells are on a micrometric scale.

The test cells may, in both instances, be placed directly at the free surface of one or other of the substrates, that is to say at the bond interface 10. In particular, the test cells may be flush with the free surface of one or other of the substrates (that is to say that the distance 'e' is zero or virtually zero), or may even comprise a portion emerging from the free surface. It is then possible to omit the bond layer, that is to say that the test cells are no longer buried.

The bonded substrates 1 and 8 form a structure in which the second substrate 8 is bonded to the first substrate 1 at the bond interface 10.

Figure 4:
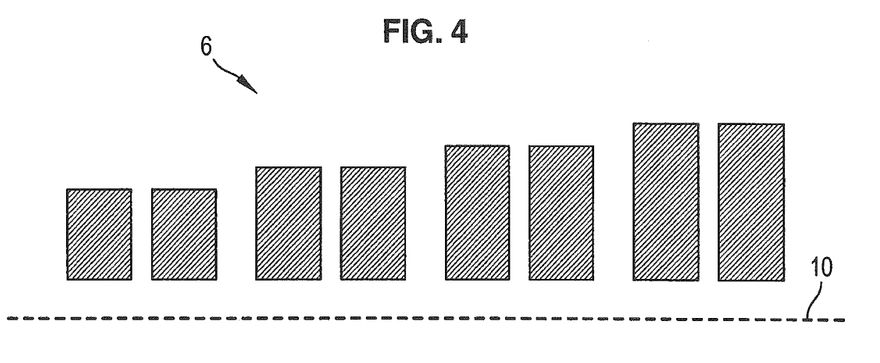
FIG. 4 shows an embodiment of a juxtaposition of elementary test cells that can be used in a substrate of FIG. 1.

In general, as shown in FIG. 4, each elementary test cell 6 is sized to apply a preset stress, at a preset temperature, to the bond interface 10. An elementary test cell 6 may for example apply a stress, σ, of 100 MPa at 300° C.

If the stress σ applied locally by the cells 6 is greater than the local adhesion energy at a given temperature T, the bond interface 10 debonds in the region located above the test cell 6, allowing the local adhesion energy at the temperature T to be determined. Generally, this will be the regions ($12_1$ to $12_4$) of the bond interface 10 located plumb with the test cell 6 in the transverse direction, such that the debonded region is associated with a particular test cell.

For example, each cell 6 comprises two pads 13, 14 of a material, such as copper, that expands when heated. By "pad" a generally cube shaped or parallelepiped shaped structure is meant. In general, the material of each cell is chosen to have a thermal expansion coefficient different from thermal expansion coefficient of the test layer 3, which is for example an oxide layer. However, the number of pads may vary and, more generally, the cell may have any appropriate structure allowing the desired result to be obtained.

Advantageously, the test layer 3 comprises a plurality of test cells 6 each sized, as shown in FIG. 4, to apply a different stress.

Figure 5:
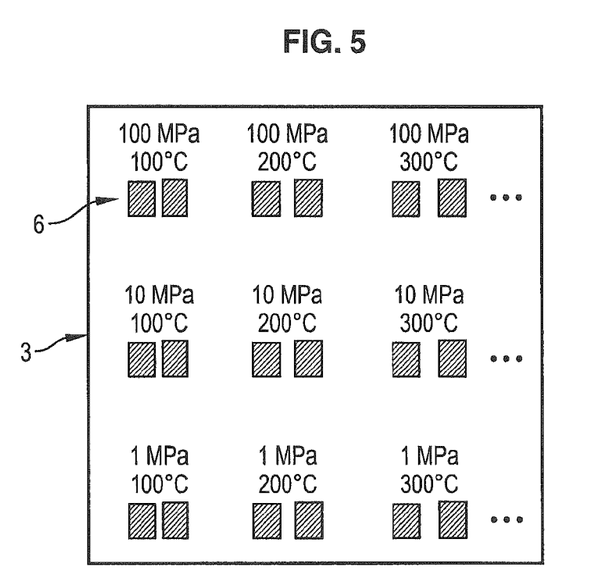
FIG. 5 shows an embodiment of a plurality of elementary test cells differentiated by the preset stress and preset temperature associated with each of the cells.

Advantageously, each elementary test cell 6 is capable of applying a preset stress at a preset temperature and the set of parameters, consisting of the preset stress and the preset temperature, is different from one cell to another, as illustrated in FIG. 5. As will be explained in the following, increasing the number of test cells 6 allows an increase in the adhesion-energy resolution at each test temperature ($T_t$) applied to the structure comprising the first 1 and the second 8 substrates.

For example, one cell may be characterized by the fact that it applies a stress of 100 MPa at a temperature of 200° C.

These values are preset and known to the operator through the choice and the dimensions of the test cells.

Figure 6:
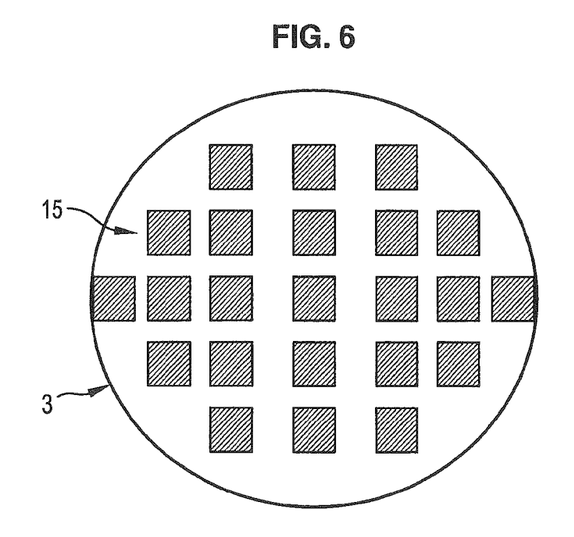
FIG. 6 shows an embodiment of test structures each comprising a plurality of elementary test cells.

In a preferred embodiment, the test layer 3 comprises a plurality of test structures 15 capable of applying stresses to a plurality of different regions of the bond interface 10, each test structure 15 comprising a plurality of different elementary test cells 6. Advantageously, each elementary test cell of a test structure is capable of applying a preset stress at a preset temperature, the set comprising the stress and the temperature being different from one cell to another in a given test structure.

This leads to duplication of the plurality of test cells 6, as for example the test cells 6 shown in FIG. 5, in several regions of the test layer 3, thereby forming test structures. By virtue of this configuration, it is possible to measure the local adhesion energy of several regions of the bond interface 10. In general, a test structure has a surface area of about 0.5 cm². Therefore, for each region covered by a test structure 15, a local adhesion energy value is obtained at various temperatures. It is clear that the greater the number of test structures 15, the greater will be the number of regions of the bond interface 10 of which the adhesion energy can be known.

Figure 7:
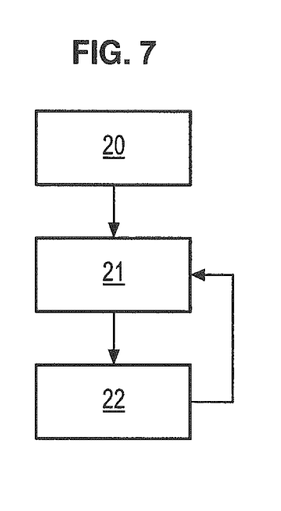
FIG. 7 shows an embodiment of a process for measuring the adhesion energy according to a second aspect of the invention.

One embodiment of a process for measuring an adhesion energy according to an aspect of the invention, implementing the substrate 1 described above, is now described.

In a first step 20, either the exposed surface of bond layer 4 or test layer 3 of the substrate 1 is bonded to a second substrate 8 in a transverse direction. This type of bonding is widely known to those skilled in the art and details are not given here.

The structure comprising the bonded substrate 1 and the bonded substrate 8 is then heat treated (step 21).

This is a treatment in which the temperature of the substrate 1, substrate 8 and interface 10 therebetween is increased up to a test temperature ($T_t$). This increase in temperature, applied to the structure, is performed in an oven in a known manner.

During the temperature increase, and as described above, the test cells 6 of the test layer 3 then apply a transverse tensile stress to the bond interface 10 located between the substrate 1 and the substrate 8. Dependent on the test temperature ($T_t$) applied to the structure comprising the substrate 1 and the substrate 8 only certain test cells will apply a particular stress, the stress being preset and specific to each cell, as shown in FIG. 5.

Indeed, the test structures 15 of the test layer 3 are sized so that each elementary test cell 6 of the test structure applies a preset stress at a preset temperatures during step 21 of applying a test temperature ($T_t$), the set consisting in the preset stress and the preset temperature (T) being different from one cell 6 to another.

It should be noted that the heat treatment described above is commonly used to strengthen the bond between two substrates 1, 8 since the room temperature bond of two substrates does not generally provide sufficient mechanical strength to meet the requirements of the electronic or microelectronic industry. The invention therefore uses this bond-strengthening step as a test step, thereby avoiding the addition of new costly steps harmful to the structure being tested, as are used in the processes of the prior art.

In certain cases at least one of the substrates 1 and/or 8 is provided with electronic circuits. For example, the 3D-integration fabrication process, consisting in bonding together substrate layers comprising electronic circuits and in connecting the circuits so as to form an electronic component, is known. Such bonding most often comprises a heat treatment step.

The test structures are in this case integrated into the electronic circuits that conventionally contain at their periphery, generally on the cleavage lines, a number of test and measurement structures for the monitoring process.

Advantageously, the regions of the interface 10 provided with test cells may be placed on cleavage lines of post-bond substrates.

The adhesion energy test structures according to the invention are very easy to integrate, particularly by modifying a set of masks.

One advantage of this solution is that it constitutes a means of directly checking the adhesion energy during the 3D-integration fabrication process, and therefore enables possible fabrication defects or problems to be detected. In particular, this solution uses the heat treatment step necessary for bonding layers comprising electronic circuits to characterized the adhesion energy.

In a subsequent step 22, the bond interface 10 is observed. The debonded and/or defective regions of the bond interface 10 are identified and indicate that the local adhesion energy has been reached or exceeded.

Figure 8:
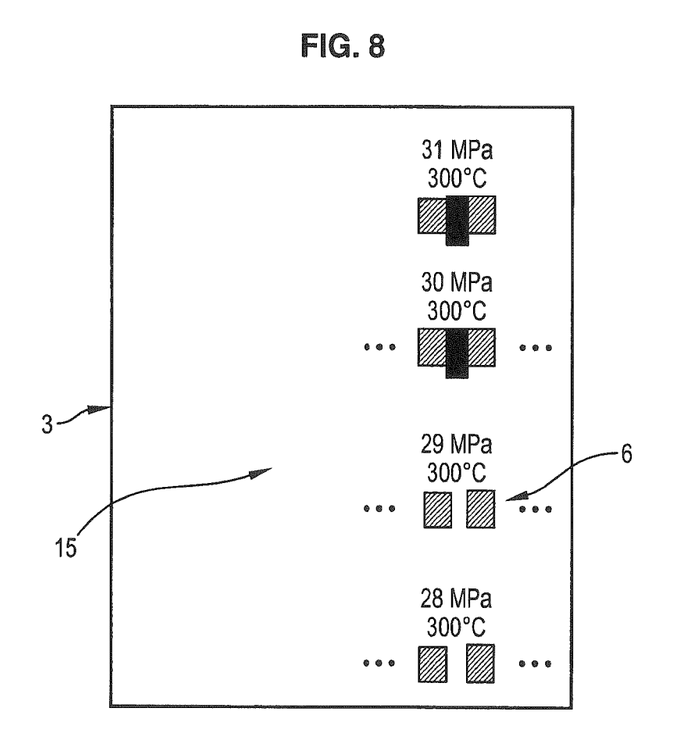
FIG. 8 shows schematically a principle for observing test cells after a heat treatment step.

The local adhesion energy in each region of the bond interface 10 is deduced from the stress applied by the test cell 6 or test cells 6 that caused the region to debond, as illustrated in FIG. 8. The test cells 6 in FIG. 8 form a test structure 15.

The defective and/or debonded regions of the bond interface 10 are identified, thereby enabling the test cells 6 that have caused a debond (schematized by a black rectangle in FIG. 8) to be identified. In the case of pads, the debond occurs in the region of the bond interface located between the pads.

For example, in FIG. 8, a test temperature ($T_t$) of 300° C. has been applied to the structure comprising the first substrate 1 and the second substrate 2. It is then noticed that the bond interface 10 has debonded only at the cells of the structure 15 that are sized to apply stresses at 300° C. that are greater than the local bonding energy.

It is therefore deduced from this that the stress that caused a debond of the corresponding region of the bond interface 10 is between 29 MPa and 30 MPa at 300° C.

This makes it possible, in particular from graphs showing the relationship between stress, temperature and energy, to deduce the local adhesion energy at a given temperature in the region of the bond interface located plumb with the test structure 15 in the transverse direction. These graphs are based on models that take into account the different parameters implemented in the process: stress, temperature, type of material etc.

In the case of FIG. 8 described above, and from the stress determined as explained above, it is possible to deduce from this the local adhesion energy at 300° C. in the debonded region.

The local adhesion energy in a region of the bond interface 10 is therefore advantageously deduced from the stress applied by the test cells 6 that caused a debond in the region.

It is understood that the greater the number of test cells for a given test structure the greater will be the number of measurement points. In particular, having a large number of different preset-stress/preset-temperature pairs increases the measurement resolution. The local adhesion-energy resolution at each temperature is therefore increased.

Likewise, having a plurality of test structures themselves comprising a plurality of elementary test cells 6 enables the local adhesion energy to be determined in a large number of regions of the bond interface 10.

Advantageously, steps 21 and 22 may be repeated iteratively, in the case of an increasing temperature. In particular, the sequence comprising the steps consisting in applying a test temperature ($T_t$) to the first and second substrates and identifying the debonded regions of the bond interface is repeated in a range comprising several test temperatures ($T_t$), so as to deduce the local adhesion energy for the range of test temperatures. A series of discrete measurements is then obtained, which enables an adhesion energy variation curve to be drawn as a function of the temperature for each region of the bond interface 10 studied. However, this principle is relevant only when a gradual increase in temperature is applied during the successive tests.

In practice a new test temperature ($T_t$) is applied to the first 1 and second 8 substrates bonded to each other, then the bond interface 10 is observed. This sequence is repeated as many times as necessary.

The invention provides a measurement of the local adhesion energy in different regions of the bond interface 10.

The observation of bond interface 10 defects may be carried out using any technique known to a person skilled in the art.

Advantageously, regions of the bond interface 10 may be observed, after annealing, by SAM (scanning acoustic microscope). However it is also envisaged that interface defects be observed in real time, that is to say at the same time as the test temperature is applied to the bonded substrates.

In another advantageous embodiment, each cell is physically differentiated by a set of parameters comprising the preset stress applied by the cell and the preset temperature at which the stress is applied, as illustrated in FIG. 8, and/or a set of parameters comprising the local adhesion energy and the temperature at which the energy is reached. These data are etched or scribed near each cell.

Thus, the local adhesion energy is deduced by reading the set directly for each cell associated with a debonded region.

Advantageously, the support layer 2 is transparent and this enables the stress or the adhesion energy to be read directly with a microscope. For example a layer of glass or quartz may be used.

The invention may advantageously be used for testing or for monitoring the bond in the context of a 3D integration of substrates.

The test cells are identical to those described in the aforementioned embodiments and may be placed, in the form of distributed test structures, at the free surface of the substrate.

In the case of 3D integration, it is furthermore possible for the substrate comprising the test cells to furthermore comprise electronic circuits. This is equally applicable whether the substrates are bonded via a bond layer (also known to those skilled in the art as a "blanket") or not, that is to say that the substrates are directly assembled at their top layer comprising electronic circuits.

Generally, the measurements obtained with the process according to the invention are precise and are an improvement on the results of the prior art, like for example the results obtained with the process proposed by Maszara.

In addition, the invention provides a simple and direct measurement of the adhesion energy of the bond interface. Furthermore, the invention provides a measurement of the adhesion energy at various temperatures.

Finally, the process according to the invention is advantageous as it is not very invasive. An operator wishing to measure the energy of adhesion between two substrates to be bonded may easily utilize the substrate according to the invention that comprises all the functional layers necessary for a given application (bond layer and support substrate) and differs only by the presence of test cells, buried or not. In addition, the process requires only a few additional steps beyond the conventional steps of bonding and of bond-strengthening by heating of the bonded substrates.

The invention is therefore very advantageous both in terms of its flexibility and in terms of its cost.

What is claimed is:

1. A process for measuring an energy of adhesion between two bonded substrates which comprises:
   providing a test layer on a first substrate, wherein the test layer has an exposed surface;
   providing a plurality of elementary test cells within the test layer for locally applying a preset mechanical stress ($\sigma$) dependent on a temperature (T);
   bonding a second substrate to the exposed surface of the test layer to form a bonding interface; and
   increasing the temperature (T) of the bonded substrates to up to a test temperature ($T_t$), wherein the plurality of elementary test cells apply a preset transverse tensile stress to the bond interface so as to deduce the adhesion energy.

2. The process of claim 1, which further comprises providing a bonding layer on the exposed surface of the test layer, and bonding the second substrate to the surface of the bonding layer, such that the bonding layer is between the second substrate and the test layer and test cells within the test layer.

3. The process of claim 1, which further comprises
   applying the test temperature to the substrates, wherein each of the plurality of elementary test cells apply a different preset mechanical stress ($\sigma$), at the test temperature ($T_t$) locally to the bond interface in the transverse direction at the bond interface between the substrates in a direction tending to separate the bonded surfaces; and
   identifying debonded regions at the bond interface associated with one or more elementary test cells applying the different preset mechanical stress ($\sigma$), such that the local adhesion energy at the test temperature in the regions may be deduced from which test cells are associated with a debonded region.

4. The process of claim 3, which further comprises:
   repeating the steps of applying a test temperature ($T_t$) to the substrates over a range of temperatures (T); and
   identifying the debonded regions of the bond interface at the several different test temperatures ($T_t$) in the range, so as to deduce the adhesion energy over the range of temperatures.

5. The process of claim 3, in which the debonded regions of the bond interface are identified using an acoustic microscope.

6. The process of claim 1, wherein each elementary test cell within the test layer comprises two pads where both pads are made of a material that expands when heated, and further wherein each test cell applies a different preset mechanical stress ($\sigma$) at the same test temperature ($T_t$), compared to the other test cells within the test layer.

7. The process of claim 6, wherein a plurality of elementary test cells forms a test structure, and each test cell within the test structure applies a different preset stress at the same preset test temperature, such that the test structure indicates the local adhesion energy at the bond interface by identifying the debonded regions between one test cell and another.

8. The process of claim 7, wherein the test layer comprises a plurality of test structures distributed over the surface of the first substrate so as to apply stresses to a plurality of different regions of the bond interface, wherein each test structure comprises a plurality of elementary test cells that apply a different preset mechanical stress at the same test temperature.

9. The process of claim 7, wherein each test cell is physically differentiated from the other test cells in a test structure by a set of parameters comprising a preset stress applied by the cell and a preset temperature at which the stress is applied, or a local adhesion energy and a temperature at which the adhesion energy is reached; and the process further comprises the step of deducing the adhesion energy by determining which test cells with a preset set of parameters are associated with a debonded region.

10. A substrate capable of measuring an energy of adhesion between itself and another substrate at a bond interface comprising:
- a first substrate;
- a test layer formed on the first substrate, wherein the test layer has an exposed surface for bonding;
- a plurality of elementary test cells formed within the test layer for locally applying in a transverse direction, a preset mechanical stress ($\sigma$) dependent on the temperature (T), to a bond interface located between the surface of the test layer and another substrate bonded thereto.

11. The substrate of claim 10, further comprising:
- a second substrate bonded to the exposed surface of the test layer to form a bond interface, wherein the test layer and bond interface are at a test temperature; and
- locally debonded regions at the bond interface, wherein one of the debonded regions is associated with one elementary test cell applying the preset mechanical stress ($\sigma$) at the test temperature ($T_t$), where the preset mechanical stress is different from one elementary test cell to another at the test temperature, such that the local adhesion energy in a region may be determined by which test cell is associated with a debonded region.

12. The substrate of claim 10, further comprising a bond layer formed on the surface of the test layer, such that the bonding layer is between the second substrate and the test layer, wherein the test cells are distributed in the test layer and covered by the bond layer, and a surface of the bond layer forms the bond interface with the second substrate.

13. The substrate of claim 10, wherein the first substrate is a transparent support layer upon which the test layer and elementary test cells are formed.

14. The substrate of claim 10, wherein the elementary test cells are at the free surface of the test layer, such that the test cells apply the preset mechanical stress to the second substrate at the bond interface.

15. The substrate of claim 10, further comprising a plurality of test structures wherein each test structure has a plurality of different elementary test cells capable of applying different mechanical stresses to a plurality of regions of the bond interface at a preset temperature.

16. The substrate of claim 10, wherein each elementary test cell within the test layer comprises two pads where both pads are made of a material that expands when heated.

17. The substrate of claim 11, in which each cell is physically differentiated by a set of parameters comprising a preset stress applied by the cell and a preset temperature at which the stress is applied, or a local adhesion energy and a temperature at which the energy is reached.

18. The substrate of claim 11, wherein at least the first substrate or the second substrate include electronic circuits.

19. The substrate of claim 11, associated with an acoustic microscope for identifying debonded regions.

* * * * *